(12) United States Patent
Shen et al.

(10) Patent No.: US 12,741,268 B2
(45) Date of Patent: Sep. 22, 2026

(54) COMPOSITE CATALYST AND USE THEREOF IN PREPARING PROPYLENE GLYCOL

(71) Applicant: TONGJI UNIVERSITY, Shanghai (CN)

(72) Inventors: Zheng Shen, Shanghai (CN); Yalei Zhang, Shanghai (CN); Minyan Gu, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 999 days.

(21) Appl. No.: 17/913,164

(22) PCT Filed: May 27, 2020

(86) PCT No.: PCT/CN2020/092617
§ 371 (c)(1),
(2) Date: May 31, 2023

(87) PCT Pub. No.: WO2021/036374
PCT Pub. Date: Mar. 4, 2021

(65) Prior Publication Data

US 2023/0285939 A1 Sep. 14, 2023

(30) Foreign Application Priority Data

Aug. 26, 2019 (CN) ........................ 201910788729.2

(51) Int. Cl.
*B01J 23/02* (2006.01)
*B01J 23/42* (2006.01)
(Continued)

(52) U.S. Cl.
CPC .............. *B01J 23/02* (2013.01); *B01J 23/42* (2013.01); *B01J 23/44* (2013.01); *B01J 23/464* (2013.01);
(Continued)

(58) Field of Classification Search
CPC ... B01J 21/08; B01J 23/02; B01J 23/42; B01J 23/44; B01J 23/464; B01J 23/58;
(Continued)

(56) References Cited

FOREIGN PATENT DOCUMENTS

| | | |
|---|---|---|
| CN | 103159587 A | 6/2013 |
| CN | 110483239 A | 11/2019 |

(Continued)

OTHER PUBLICATIONS

Zhang, M., et al., 2015, ACS Applied Materials & Interfaces, 7, 1533-1540. <DOI: 10.1021/am506643b> (Year: 2015).*
(Continued)

*Primary Examiner* — Brian A Mccaig
(74) *Attorney, Agent, or Firm* — IPRTOP LLC

(57) ABSTRACT

The present application provides a composite catalyst and use thereof in preparing propylene glycol, where the composite catalyst includes: a main catalyst; and an assistant catalyst, forming on the main catalyst; the assistant catalyst is a magnesium hydroxide shell with a cage-like shape forming on the surface of the main catalyst, and the main catalyst is located inside the magnesium hydroxide shell.

16 Claims, 8 Drawing Sheets mixing a sugar, a main catalyst and an assistant catalyst in a reactor — S1 performing a hydrothermal reaction in the reactor under a reducing gas atmosphere to obtain the propylene glycol — S2

(51) Int. Cl.

| | |
|---|---|
| ***B01J 23/44*** | (2006.01) |
| ***B01J 23/46*** | (2006.01) |
| ***B01J 35/30*** | (2024.01) |
| ***B01J 35/45*** | (2024.01) |
| ***B01J 35/61*** | (2024.01) |
| ***B01J 35/64*** | (2024.01) |
| ***C07C 29/60*** | (2006.01) |

(52) U.S. Cl.

CPC ............. *B01J 35/393* (2024.01); *B01J 35/45* (2024.01); *B01J 35/613* (2024.01); *B01J 35/615* (2024.01); *B01J 35/617* (2024.01); *B01J 35/643* (2024.01); *B01J 35/647* (2024.01); *B01J 35/651* (2024.01); *C07C 29/60* (2013.01); *B01J 2235/30* (2024.01)

(58) Field of Classification Search

CPC ........ B01J 35/393; B01J 35/45; B01J 35/613; B01J 35/615; B01J 35/617; B01J 35/643; B01J 35/651; B01J 37/0201; B01J 37/0205; B01J 37/18; C07C 29/00; C07C 29/60; Y02P 20/52

See application file for complete search history.

(56) References Cited

FOREIGN PATENT DOCUMENTS

| | | |
|---|---|---|
| JP | 2007283175 A | 11/2007 |
| WO | 2009151021 A1 | 12/2009 |

OTHER PUBLICATIONS

Minyan Gu et al. "Hydrogenolysis of Glucose Into Propylene Glycol over PUSi02@Mg(OH)2 Catalyst" Chern. Cat. Chern., vol. 12. No. 13. Apr. 16, 2020 (Apr. 16, 2020). ISSN: 1867-3899. p. 3447-345. in particular abstract. p. 3448. left-hand column. paragraph 2 to p. 3449. left-hand column. paragraph 1. figures 1-2. table 1. supplemental information. page.

Jiying Sun et al. "Selective Hydrogenolysis of Biomass-Derived Xylitol to Ethylene Glycol and Propylene Glycol on Supported Ru Catalysts" Green Chern., vol. 13. No. 1 . . . Dec. 31, 2011 (Dec. 31, 2011). ISSN: 1463-9262. pp. 135-142. in particular abstract. sections 2-3. tables 1-2. figure 4.

(Yang. Long et al.). (Study on the synthesis of propylene glycol through cellulose hydrogenation using alkaline promoted Ni—W/ ~-zeo1ite catalysts) (Journal of Fuel Chemistry and Technology), vol. 45. No.1 . . . Jan. 31, 2017 (Jan. 31, 2017). ISSN: 0253-2409.

* cited by examiner

COMPOSITE CATALYST AND USE THEREOF IN PREPARING PROPYLENE GLYCOL

FIELD OF TECHNOLOGY

The present application relates to the technical field of environmental chemical industry, and in particular, to a composite catalyst and use thereof in preparing propylene glycol.

BACKGROUND

As a high value-added chemical, propylene glycol (1,2-propanediol or 1,3-propanediol) is not only a chemical product used in food, drug, cosmetics, anti-freezing mixture and other industries, but also an intermediate molecule used in the production of unsaturated resin polyester. With the growing demand in various industries, the demand for propylene glycol is increasing in the world. The traditional production method of propylene glycol in industry relies on petrochemical industry. According to the concept of sustainable development, the catalytic conversion of sugars (such as cellulose, starch, glucose, etc.) into propylene glycol can realize the green production of propylene glycol. However, at present, there are many difficulties in realizing the efficient conversion of sugars into propylene glycol through catalytic hydrogenolysis under the same catalyst conditions. Taking glucose as an example, the difficulties include: it is difficult to unidirectionally isomerize glucose to fructose; it is difficult to control the bond breaking of C6 monosaccharides into C3-C3; it is difficult to suppress side reactions; and it is difficult to control the four processes of hydrolysis, isomerization, bond breaking and hydrogenation of various initial, intermediate and final products involved in the reaction system. The above problems collectively result in low selectivity and yield for the conversion of sugars to propylene glycol.

SUMMARY

The present application provides a composite catalyst and use thereof in preparing propylene glycol, which realizes high selectivity and yield for the production of propylene glycol.

The present application is implemented by the following technical solutions.

The present application provides a composite catalyst, including: a main catalyst; and an assistant catalyst, forming on the main catalyst; where the assistant catalyst is a magnesium hydroxide shell with a cage-like shape forming on the surface of the main catalyst, and the main catalyst is located inside the magnesium hydroxide shell.

In one embodiment, the thickness of the assistant catalyst is 5-20 nanometers.

In one embodiment, the active components of the main catalyst include one or more selected from platinum nanoparticles, palladium nanoparticles and rhodium nanoparticles.

In one embodiment, the particle size of the active component of the main catalyst is 3-40 nanometers.

In one embodiment, the chemical valence state of the active component of the main catalyst is zero.

In one embodiment, the number of basic sites of the composite catalyst is 0.028-3.14 mmol/g.

In one embodiment, a carrier of the main catalyst includes aluminosilicate molecular sieve, silica, alumina or zirconia.

In one embodiment, an average pore size of the carrier of the main catalyst is 1-50 nanometers.

In one embodiment, the assistant catalyst includes magnesium hydroxide or magnesium oxide.

In one embodiment, the specific surface area of the composite catalyst is 20-600 $cm^2/g$.

The present application further provides a composite catalyst, including: a main catalyst; and an assistant catalyst, forming on the main catalyst; where the assistant catalyst is a magnesium hydroxide shell with a cage-like shape forming on the surface of the main catalyst, and the main catalyst is located inside the magnesium hydroxide shell; where the magnesium hydroxide is in the form of sheets to coat the main catalyst.

The present application further provides a method for preparing propylene glycol, at least including: mixing a sugar, a main catalyst and an assistant catalyst in a reactor; performing a hydrothermal reaction in the reactor under a reducing gas atmosphere to obtain the propylene glycol, where the assistant catalyst is a magnesium hydroxide shell with a cage-like shape forming on the surface of the main catalyst, and the main catalyst is located inside the magnesium hydroxide shell to form a main catalyst-assistant catalyst composite catalyst with catalytic activity.

In one embodiment, the main catalyst-assistant catalyst composite catalyst has a core-shell structure.

In one embodiment, the amount of the sugar is 10-22.5 mg/ml.

In one embodiment, the temperature of the hydrothermal reaction in the reactor is 140° C.-250° C., and the pressure of the reducing gas atmosphere is 2-6 MPa. The reducing gas includes hydrogen.

In one embodiment, the reactor includes a tank reactor or a fixed bed reactor.

In one embodiment, in the tank reactor, the amount of the assistant catalyst is 0.5-2 mg/mL, and the mass ratio of the main catalyst to the assistant catalyst is 10-40:1.

In one embodiment, the space velocity in the fixed bed reactor is 0.12 $h^{-1}$ to 0.96 $h^{-1}$.

In one embodiment, the sugar in the tank reactor includes one or more selected from glucose, sucrose, fructose, trehalose, maltose, starch, and cellulose.

In one embodiment, the sugar in the fixed bed reactor includes one or more selected from glucose, sucrose, fructose, trehalose, and maltose.

In one embodiment, in the tank reactor, the reaction conditions further include a reaction time of 0.5-6 hours and a stirring rate of 200-600 rpm.

In one embodiment, a method for preparing the main catalyst incudes: performing a saturated water absorption measurement on a carrier; dissolving a precursor containing the active component of the main catalyst in deionized water to obtain an aqueous precursor solution; adding the carrier to the aqueous precursor solution to obtain a main catalyst intermediate; aging, drying and calcining the main catalyst intermediate to obtain a main catalyst in an oxidized state; performing a reduction treatment on the main catalyst in the oxidized state to obtain the main catalyst; where the ratio of the volume of the deionized water to the mass of the carrier is equal to the saturated water absorption rate, and the loading of the active components of the main catalyst is 0.5%-10%.

Therefore, on the one hand, the aqueous precursor solution can be completely absorbed into pores in the carrier during an impregnation process, which is conducive to the uniform dispersion of the active metals. On the other hand, the active metal can play a better hydrogenation catalytic effect within the loading range of 0.5-10%.

In one embodiment, the temperature for performing the reduction treatment is 80-300° C.

In the present application, the magnesium hydroxide shell with the cage-like shape is formed on the surface of the main catalyst by in-situ loading to form a main catalyst-assistant catalyst composite catalyst with special structure and catalytic activity, which can control a reaction system to proceed in the direction of producing propylene glycol, thereby greatly improving the selectivity of propylene glycol. The core-shell structure of the composite catalyst of the present application can ensure that tandem reactions occur in sequence, specifically, the assistant catalyst can promote the isomerization of glucose into fructose, then promote the reverse aldol condensation reaction of fructose to generate glyceraldehyde and dihydroxyacetone, and after a further series of processes, the hydrogenation reaction finally occurs on the main catalyst to generate propylene glycol. The magnesium hydroxide shell of the present application has many advantages, such as its loose structure and its gap, which will not prevent the reactants from reaching the inside of the composite catalyst for catalytic reaction. In addition, the magnesium hydroxide shell of the present application can keep the composite catalyst stable during repeated use, reduce the loss of active metal nanoparticles such as Pt nanoparticles, and maintain a high yield of propylene glycol during repeated reuse. Compared with traditional petrochemical methods, the method for preparing propylene glycol described in this application has the advantages of being green, sustainable and environmentally friendly, and can realize the directional conversion of sugar biomass into propylene glycol, thus providing technical support for a new industrialized path for propylene glycol production.

DESCRIPTION OF THE DRAWINGS

In order to explain the specific embodiment of this application or the technical solution in the existing technology more clearly, the specific embodiment or the existing technology will be briefly introduced below through the following drawings. Obviously, the drawings in the following description are some embodiments of this application. For the ordinary skilled in the art, other drawings can also be obtained according to these drawings.

DETAILED DESCRIPTION

The technical solutions of the present application will be clearly and completely described below with reference to the accompanying drawings. Obviously, the described embodiments are part of the embodiments of the present application, but not all of the embodiments. Based on the embodiments in the present application, all other embodiments obtained by those of ordinary skill in the art without creative efforts shall fall within the protection scope of the present application.

In the description of this application, it should be noted that when the terms “center”, “up”, “below”, “left”, “right”, “vertical”, “horizontal”, “inside”, “outside” etc. appear, the indicated orientation or positional relationship is based on the drawings, which is only for the convenience of describing the present application and simplifying the description, rather than indicating or implying that the related device or element must have a specific orientation, a construction in specific orientation, or be operated in a specific orientation, and therefore it should not be construed as limitations on this application. Furthermore, the terms “first” and “second”, as they appear, are only used for describing and should not be construed as indication or implication of a priority of importance. Therein, the terms “first position” and “second position” are two different positions.

In the description of this application, it should be noted that, unless otherwise specified and limited, the terms “installed”, “connected” and “connection” should be understood in a broad sense, for example, it may be a fixed connection or a detachable connection or an integral connection; may be a mechanical connection or an electrical connection; or may be a direct connection or an indirect connection through an intermediate medium, or may be an internal communication between two elements. For those of ordinary skill in the art, the specific meanings of the above terms in this application can be understood in specific situations.

When numerical ranges are given in the description, it should be understand that, unless otherwise indicated herein, both endpoints of each numerical range and any number between the two endpoints may be selected for use. Unless otherwise defined, all technical and scientific terms used in this application have the same meaning as understood by those skilled in the art from the prior art, and the present application can also be implemented by any methods, devices and materials of the prior art similar or equivalent to those described in the embodiments In the present application, a magnesium hydroxide shell with a cage-like shape is formed on the surface of a main catalyst by in-situ loading to form a main catalyst-assistant catalyst composite catalyst with special structure and catalytic activity, which can control the reaction system to proceed in the direction of producing propylene glycol, thus greatly improving the selectivity of propylene glycol.

Figure 1:
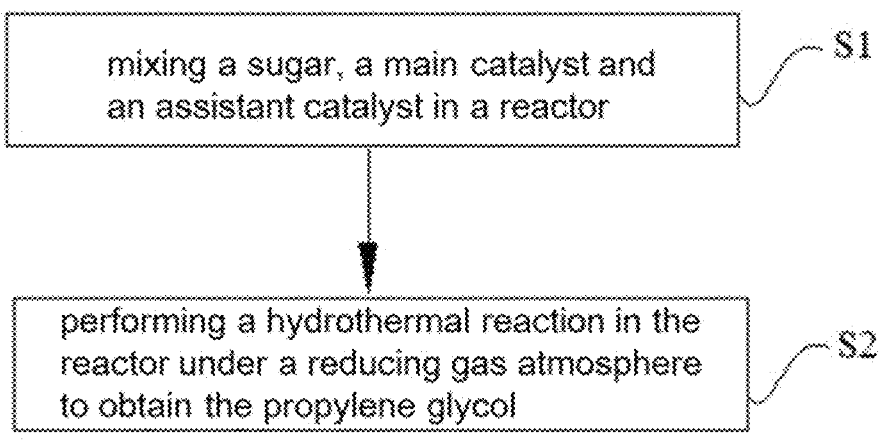
FIG. 1 is a schematic process diagram of a method for preparing propylene glycol in one embodiment.

As shown in FIG. 1, the present application provides a method for preparing propylene glycol, the method at least includes: S1. mixing a sugar, a main catalyst and an assistant catalyst in a reactor; S2. performing a hydrothermal reaction in the reactor under a reducing gas atmosphere to obtain the propylene glycol, where the assistant catalyst is a magnesium hydroxide shell with a cage-like shape forming on the surface of the main catalyst, and the main catalyst is located inside the magnesium hydroxide shell to form a main catalyst-assistant catalyst composite catalyst with catalytic activity.

Specifically, in S1, the sugar, the main catalyst and the assistant catalyst are formed into a mixed system in the reactor, where the reactor is selected from a tank reactor and a fixed bed reactor. For example, in the tank reactor, the amount of the sugar is 10-22.5 mg/ml, and the mass ratio of the main catalyst to the assistant catalyst is 10-40:1. In the tank reactor, the sugar includes one or more selected from glucose, sucrose, fructose, trehalose, maltose, starch, and cellulose. For example, in the fixed bed reactor, the sugar includes one or more selected from glucose, sucrose, fructose, trehalose, and maltose. The assistant catalyst includes, for example, magnesium oxide or magnesium hydroxide.

Specifically, in S1, a method for preparing the main catalyst, for example, includes: performing a saturated water absorption measurement on a carrier; dissolving a precursor containing the active component of the main catalyst in deionized water to obtain an aqueous precursor solution; adding the carrier to the aqueous precursor solution to obtain a main catalyst intermediate; aging, drying and calcining the main catalyst intermediate to obtain a main catalyst in an oxidized state; performing a reduction treatment on the main catalyst in the oxidized state to obtain the main catalyst. The ratio of the volume of the deionized water to the mass of the carrier is equal to the saturated water absorption rate, and the loading of the active components of the main catalyst is 0.5%-10%. Therefore, on the one hand, the aqueous precursor solution can be completely absorbed into pores in the carrier during an impregnation process, which is conducive to the uniform dispersion of the active metals. On the other hand, the active metal can play a better hydrogenation catalytic effect within the loading range of 0.5-10%. The temperature for performing the reduction treatment is 80-300° C. The time of the aging is at least 6 hours, the time of the drying is at least 6 hours, the temperature of the calcining is 400-450° C., and the time of the calcining is 4-8 hours. Operation conditions for the calcining also include performing in a tube furnace under static air, and the heating rate is 1-2° C./min. In one embodiment, the active component of the main catalyst includes, for example, one or more selected from platinum nanoparticle, palladium nanoparticle, cobalt nanoparticle, rhodium nanoparticle, iridium nanoparticle, silver nanoparticle and gold nanoparticle. The carrier of the main catalyst includes, for example, one of aluminosilicate molecular sieve, silica, alumina, zirconia, and silicon carbide.

Figure 3:
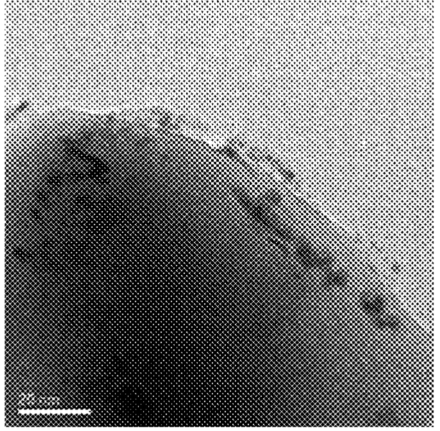
FIG. 3 is a TEM image of the PtNPs/$SiO_2$ main catalyst at another magnification in one embodiment.
Figure 14:
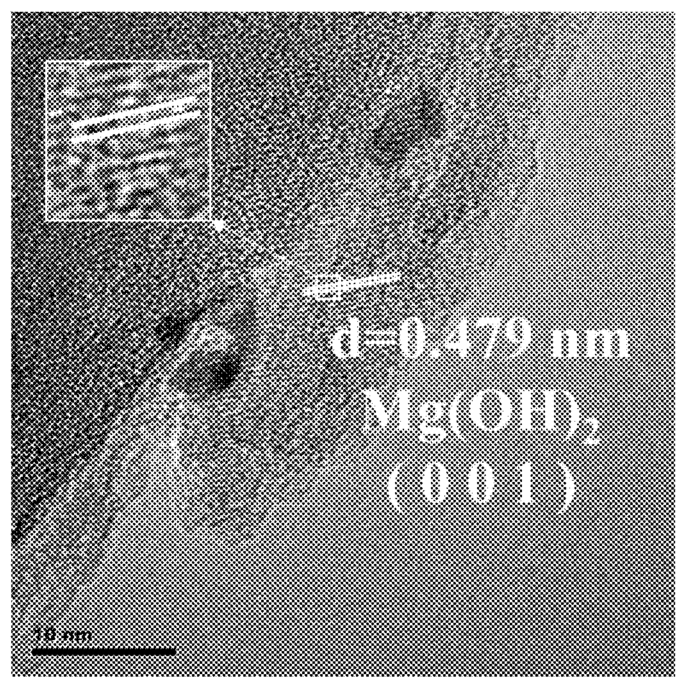
FIG. 14 is a high-resolution TEM image of the composite catalyst in one embodiment.

Specifically, in S2, the mixed system obtained in S1 is subjected to the hydrothermal reaction under the reducing gas atmosphere to obtain the propylene glycol, where the assistant catalyst is the magnesium hydroxide shell coated on the surface of the main catalyst, and the magnesium hydroxide is in the form of sheets to coat the main catalyst to form a main catalyst-assistant catalyst composite catalyst with catalytic activity. The formation of sheet-like $Mg(OH)_2$ is attributed to the preferential crystal growth of (001) planes under hydrothermal conditions, where the high temperature provides more energy to facilitate the formation of Mg—OH ionic bonds, thereby promoting the growth of (001) planes. Further, the assistant catalyst is the magnesium hydroxide shell with the cage-like shape forming on the surface of the main catalyst, and the main catalyst is located inside the magnesium hydroxide shell. For example, a reaction is performed in the tank reactor filled with hydrogen and under the following conditions: a reaction temperature of 140° C.-250° C., a reaction time of 0.5-6 hours, a hydrogen pressure of 2-6 Mpa, and a stirring rate is 200-600 rpm. In one embodiment, a reaction is performed in the tank reactor in S2, and the assistant catalyst includes magnesium oxide or magnesium hydroxide. In the tank reactor, the magnesium oxide or magnesium hydroxide forms the magnesium hydroxide shell with the cage-like shape on the surface of the main catalyst during the reaction process, thus forming the main catalyst-assistant catalyst composite catalyst that can catalyze the reaction. Specifically, the above-mentioned main catalyst and assistant catalyst (such as powder of magnesium oxide) are added into the tank reactor, afterwards, for example, the magnesium oxide undergoes in-situ hydrolysis, recombination, and hydrothermal coating during the reaction. The temperature and stirring rate of the hydrothermal coating are consistent with those of the mixing system, where the temperature is 140° C.-250° C., and the stirring rate is 200-600 rpm. As shown in FIG. 3$F_{[ysy1]}$, it is shown that the magnesium hydroxide shell with the cage-like shape is formed on the surface of the main catalyst, where the thickness of the magnesium hydroxide shell is, for example, 5-20 nm. The particle size of the active component in the main catalyst is, for example, 3-40 nanometers. The valence state of the active component in the main catalyst is zero. The number of basic sites of the composite catalyst is, for example, 0.028-3.14 mmol/g. The specific surface area of the composite catalyst is, for example, 20-600 $cm^2/g$. As shown in FIG. 14, the lattice spacing of the magnesium hydroxide shell is 0.479 nanometers, which is consistent with that of the (001) crystal plane of magnesium hydroxide. The special structure of the composite catalyst of the present application determines the high selectivity to propylene glycol.

Figure 2:
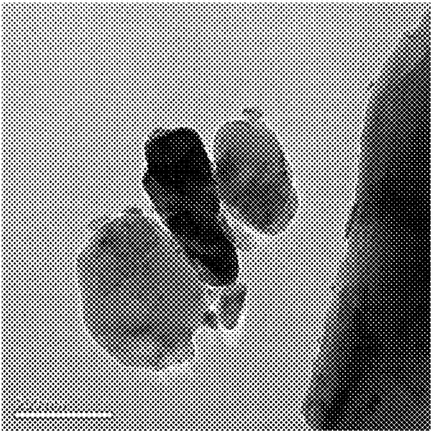
FIG. 2 is a TEM image of a PtNPs/$SiO_2$ main catalyst in one embodiment.

Referring to FIGS. 2-3, transmission electron microscopy (TEM) images of a $PtNPs/SiO_2$ main catalyst with a loading of 5% are shown. Specifically, in one embodiment, platinum nanoparticles (PtNPs) are loaded, for example, on four carriers of silica, alumina, aluminosilicate molecular sieves (such as β-molecular sieve) and montmorillonite molecular sieve (namely K-10 molecular sieve), to illustrate the method for preparing the main catalyst.

(1) Loading the Active Component on the Carrier.

Measuring the saturated water absorption rate of silica, alumina, β-molecular sieve and K-10 molecular sieve carriers. Weighing 1 g of powder of any carrier after completely dry treatment, and adding deionized water dropwise until the surface of the powder is wet and cannot absorb more water, recording the water absorption amount as a ml, that is, the saturated water absorption rate of each carrier is a ml/g.

Dissolving b mg, for example, chloroplatinic acid in c ml deionized water to prepare a homogeneous solution, adding d mg of the above carrier to the above chloroplatinic acid solution, stirring evenly, and then treating with ultrasonic for 15-20 minutes. Afterwards, aging the samples in room temperature air for more than 6 hours, and drying at 105-110° C. for more than 6 hours.

Calcining for 4-6 hours under a static air atmosphere and with a temperature of 450-500° C. in a tube furnace and the heating rate of 1-2° C./min to obtain a PtNPs/S main catalyst in the oxidized state. The above value a, b, c, and d should satisfy c/d=a, 0.37b/d=0.5%-10% (the loading of active components of the PtNPs/S main catalyst), where a is a constant.

S(2) Reducing and Activating the Main Catalyst.

Adding a certain amount of PtNPs/S catalyst and water to the reactor, and reducing the PtNPs/S main catalyst through a reduction treatment under 2-6 Mpa hydrogen pressure and with a temperature of 80-300° C. for 4-6 hours. The process of loading other active components such as palladium nanoparticles or nickel nanoparticles onto the carrier is the same as the process of loading platinum nanoparticles onto the carrier.

Figure 13:
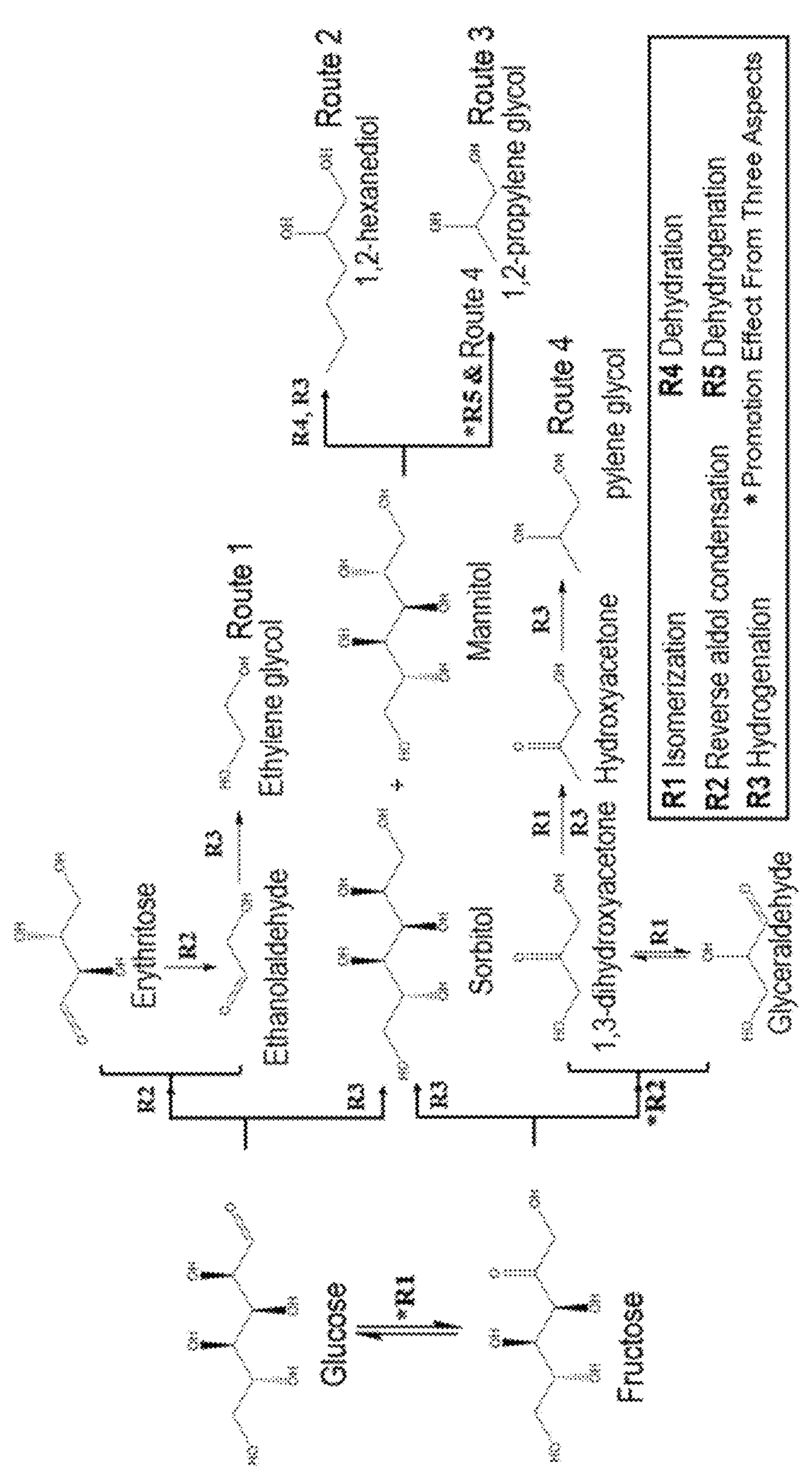
FIG. 13 shows a catalytic reaction pathway for producing propylene glycol from glucose in one embodiment.

Referring to FIG. 13, in one embodiment, selective conversion of biomass feedstocks into 1,2-propanediol through one step method is limited by a large number of side reactions and products in terms of reaction pathways and mechanisms. Taking an example of glucose as a reactant and $Pt/SiO_2@Mg(OH)_2$ as a catalyst, FIG. 13 is a diagram of the corresponding reaction path and mechanism proposed in this application. The expected path for the production of propylene glycol from glucose is as follows: the glucose is firstly isomerized into a fructose under the action of catalyst, then the fructose undergoes a reverse aldol condensation reaction to generate glyceraldehyde and dihydroxyacetone, and after follow-up processes such as hydrogenation, the production of propylene glycol is realized. The $Mg(OH)_2$ shell with the cage-like shape described in this application is a catalyst that can control the reaction to proceed in the direction of route 4 in FIG. 13, i.e., it can control the reaction by promoting the isomerization of glucose to fructose and the reverse aldol condensation reaction. In addition, the catalyst developed a dehydrogenation-reconversion route for the inevitable by-product of hexitol, which further improved the yield of propylene glycol. The promotion of the above three aspects, including isomerization of glucose to fructose, reverse aldol condensation reaction and hexitol reconversion, is the key that the $Mg(OH)_2$-based composite catalyst described in this application is superior to those of the traditional technology. In addition, the advantages of the cage-like shape structure described in this application are also reflected in the reaction process and mechanism. From the reaction path shown in FIG. 13, it can be seen that the process of converting glucose to propylene glycol is a tandem reaction process, therefore, all desired reactions need to occur in sequence, otherwise the purpose of generating propylene glycol cannot be achieved. The special structure, including the main catalyst at the inside and $Mg(OH)_2$ coated at the outside, of the composite catalyst described in this application can match the desired sequence of the tandem reaction process: first, the glucose is isomerized to the fructose under the catalysis of $Mg(OH)_2$, and then the fructose undergoes the reverse aldol condensation still under the catalysis of $Mg(OH)_2$, afterwards the intermediate product diffuses into the catalyst, and finally the final hydrogenation reaction occurs under the catalysis of PtNPs to generate propylene glycol. Therefore, the cage-like shape structure described in this application is also the key to distinguish it from the traditional technology.

The present application will be specifically described below with embodiments. The tank reactor is described by taking a stainless steel reactor as an example.

Figure 4:
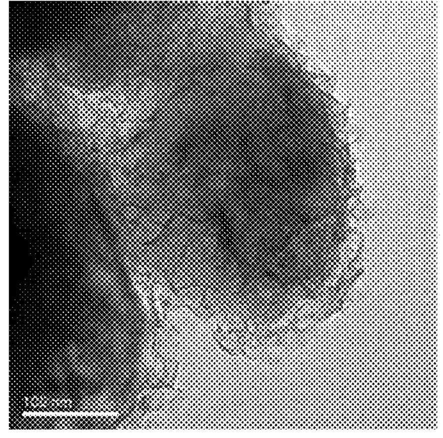
FIG. 4 is a TEM image of a PtNPs/$SiO_2$@$Mg(OH)_2$ composite catalyst in one embodiment.
Figure 5:
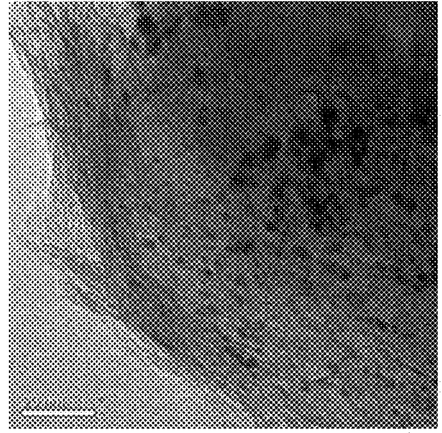
FIG. 5 is a TEM image of the PtNPs/$SiO_2$@$Mg(OH)_2$ composite catalyst at another magnification in one embodiment.

FIG. 4 and FIG. 5 show transmission electron microscopy (TEM) images of the composite catalyst with 5 wt % magnesium hydroxide loaded through in-situ hydrothermal treatment. In one embodiment, the process of in-situ hydrothermal loading of magnesium hydroxide with a mass fraction of 5%-10% (calculated as MgO) includes, 200 mg of reduced $PtNPs/SiO_2$, 10 mg of light magnesium oxide powder, 112.5 mg of, for example, glucose and 10 ml of deionized water are added to, for example, a 50 ml volume stainless steel reactor and the reactor is then sealed. An inlet valve is opened to fill with 1 Mpa hydrogen, then the hydrogen is degassed, and the above operations are repeated for 3 times to empty the air in the reactor. Finally, the reactor is filled with 5 Mpa hydrogen, and then inlet and outlet valves are closed. The reactor is heated to 180° C. for hydrothermal in-situ loading and reaction. The stirring rate is 400 rpm, and the reaction time is 4 hours (timing starts when the temperature reaches 180° C.). The solid and liquid are centrifuged after the reaction is completed and the reactor is cooled to room temperature. The liquid is analyzed by liquid chromatography and gas chromatography, and the solid is reused or characterized after being washed three times with deionized water.

Figure 6:
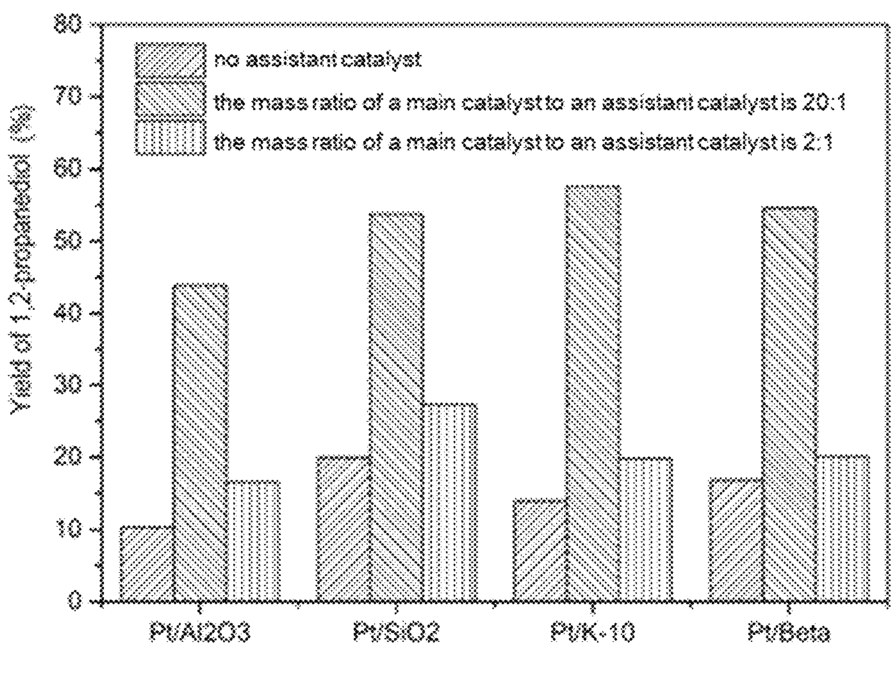
FIG. 6 shows catalytic effects of different composite catalysts in one embodiment.

FIG. 6 shows the effects of different composite catalysts on the hydrogenation of glucose to produce propylene glycol. In another embodiment, 200 mg of reduced PtNPs/$Al_2O_3$, $PtNPs/SiO_2$, PtNPs/K-10 molecular sieve or PtNPs/β molecular sieve, 10-100 mg of light magnesium oxide powder, 112.5 mg of glucose and 10-20 ml of deionized water are added to, for example, a 50 ml volume stainless steel reactor and the reactor is then sealed. An inlet valve is opened to fill with 1 Mpa hydrogen, then the hydrogen is degassed, and the above operations are repeated for 3 times to empty the air in the reactor. Finally, the reactor is filled with 5 Mpa hydrogen, and then inlet and outlet valves are closed. The reactor is heated to 180° C. for hydrothermal in-situ loading and reaction. The stirring rate is 400 rpm, and the reaction time is 4 hours (timing starts when the temperature reaches 180° C.). The solid and liquid are centrifuged after the reaction is completed and the reactor is cooled to room temperature. The liquid is analyzed by gas chromatography to obtain the yield of propylene glycol under different conditions.

Figure 7:
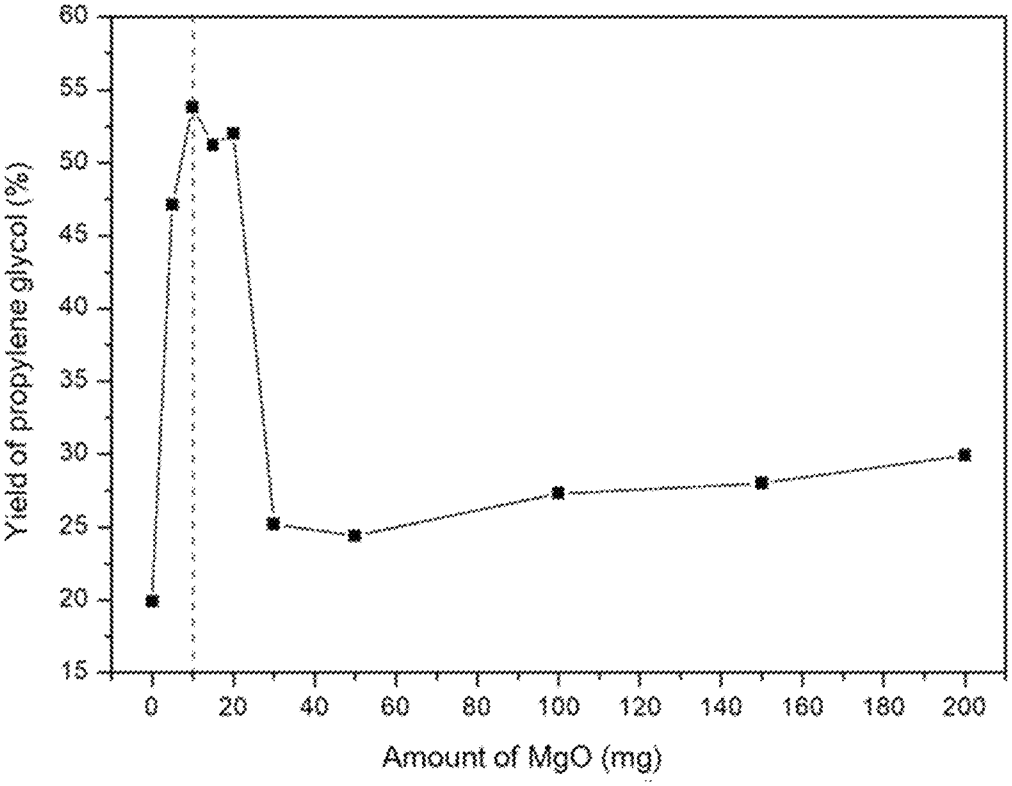
FIG. 7 shows the influence of the amount of an assistant catalyst on the production of propylene glycol from glucose in one embodiment.

FIG. 7 shows the effects of different amount of assistant catalyst on the catalytic hydrogenation of glucose to produce propylene glycol. In yet another embodiment, 200 mg of reduced $PtNPs/SiO_2$, an amount such as 0 mg, 5 mg, 10 mg, 15 mg, 20 mg, 25 mg, 50 mg, 100 mg, 150 mg and 200 mg of light magnesium oxide powder, 112.5 mg of, for example, glucose and 10 ml of deionized water are added to, for example, a 50 ml volume stainless steel reactor and then the reactor is sealed. An inlet valve is opened to fill with 1 Mpa hydrogen, then the hydrogen is degassed, and the above operations are repeated for 3 times to empty the air in the reactor. Finally, the reactor is filled with 5 Mpa hydrogen, and then inlet and outlet valves are closed. The reactor is heated to 180° C. for hydrothermal in-situ loading and reaction. The stirring rate is 400 rpm, and the reaction time is 4 hours (timing starts when the temperature reaches 180° C.). The sample is centrifuged to obtain a liquid after the reaction is completed and the reactor is cooled to room temperature. The liquid is diluted 25 times with methanol solvent, and a gas chromatography test is carried out to obtain the yield of propylene glycol under different conditions. As shown in FIG. 7, when the amount of MgO is 10 mg, the yield of propylene glycol reaches 53% and is the highest. In addition, by replacing platinum nanoparticles with palladium nanoparticles, nickel nanoparticles, ruthenium nanoparticles, cobalt nanoparticles, rhodium nanoparticles, iridium nanoparticles, copper nanoparticles, silver nanoparticles or gold nanoparticles, and performing the above process, the corresponding yield of propylene glycol are 42.5%, 46.2%, 41.7%, 19.5%, 29.8%, 32.6%, 49.9%, 22.8%, and 29.7%, respectively.

Figure 8:
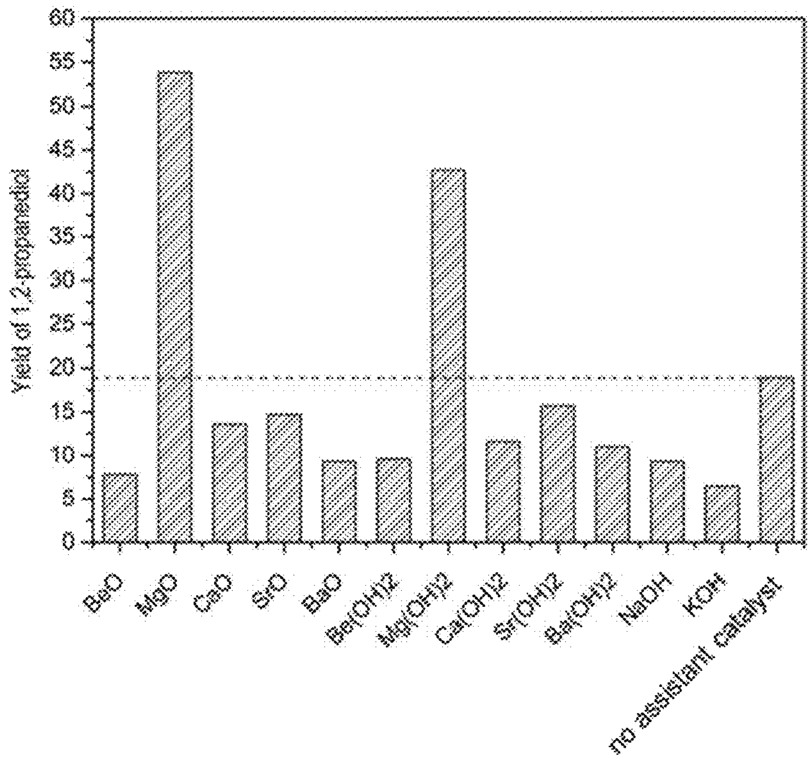
FIG. 8 shows the influence of adding different oxides and hydroxides on the production of propylene glycol from catalytic hydrogenation of glucose in one embodiment.

Referring to FIG. 8[ysy2], in yet another embodiment 112.5 mg of glucose, fructose, cellulose or mannitol, 200 mg of reduced PtNPs/$SiO_2$, 10 mg of light magnesium oxide powder and 10 ml of deionized water are added to, for example, a 50 ml volume stainless steel reactor and then the reactor is sealed. An inlet valve is opened to fill with 1 Mpa hydrogen, then the hydrogen is degassed, and the above operations are repeated for 3 times to empty the air in the reactor. Finally, the reactor is filled with 5 Mpa hydrogen, and then inlet and outlet valves are closed. The reactor is heated to 160° C.-300° C. for hydrothermal in-situ loading and reaction. The stirring rate is 200-600 rpm, and the reaction time is 0.5-6 hours (timing starts when the temperature reaches 160° C.-300° C.). The sample is centrifuged to obtain a liquid after the reaction is completed and the reactor is cooled to room temperature. The liquid is diluted 25 times with methanol solvent, and a gas chromatography test is carried out to obtain the yield of propylene glycol under different conditions. The catalytic effects of different sugar biomasses are investigated. The results show that the yield of propylene glycol from glucose under this condition is 53.8%, the yield of propylene glycol from fructose under this condition is 52.2%, the yield of propylene glycol from cellulose under this condition is 39.6%, and the yield of propylene glycol from mannitol under this condition is 27.9%.

FIG. 8 shows the effects of different oxides and hydroxides on the catalytic hydrogenation of glucose to produce propylene glycol. In yet another embodiment, 200 mg of reduced PtNPs/$SiO_2$, 10 mg of, for example, beryllium oxide (BeO), magnesium oxide (MgO), calcium oxide (CaO), tin oxide (SrO), barium oxide (BaO), beryllium hydroxide ($Be(OH)_2$), magnesium hydroxide ($Mg(OH)_2$), calcium hydroxide ($Ca(OH)_2$), tin hydroxide ($Sr(OH)_2$), barium hydroxide ($Ba(OH)_2$), sodium hydroxide (NaOH) or potassium hydroxide (KOH), 112.5 mg of, for example, glucose and 10 ml of deionized water are added to, for example, a 50 ml volume stainless steel reactor and then the reactor is sealed. An inlet valve is opened to fill with 1 Mpa hydrogen, then the hydrogen is degassed, and the above operations are repeated for 3 times to empty the air in the reactor. Finally, the reactor is filled with 5 Mpa hydrogen, and then inlet and outlet valves are closed. The reactor is heated to 160° C.-300° C. for hydrothermal in-situ loading and reaction. The stirring rate is 200-600 rpm, and the reaction time is 0.5-6 hours (timing starts when the temperature reaches 160° C.-300° C.). The sample is centrifuged to obtain a liquid after the reaction is completed and the reactor is cooled to room temperature. The liquid is diluted 25 times with methanol solvent, and a gas chromatography test is carried out to obtain the yield of propylene glycol under different conditions. As shown in FIG. 8, when MgO or magnesium hydroxide is used as an assistant catalyst, a higher yield of propylene glycol is obtained. Compared with the blank group, other oxides or hydroxides do not obtain better yields of propylene glycol. When MgO or magnesium hydroxide acts as an assistant catalyst, it is the amorphous cage-like magnesium hydroxide, which is obtained from hydrolyzing and recombining of MgO under hydrothermal conditions, has catalytic activity. Compared with the direct addition of $Mg(OH)_2$, the structure of magnesium hydroxide obtained from hydrolysis and recombination of MgO under hydrothermal conditions is more conducive to the production of propylene glycol.

Figure 9:
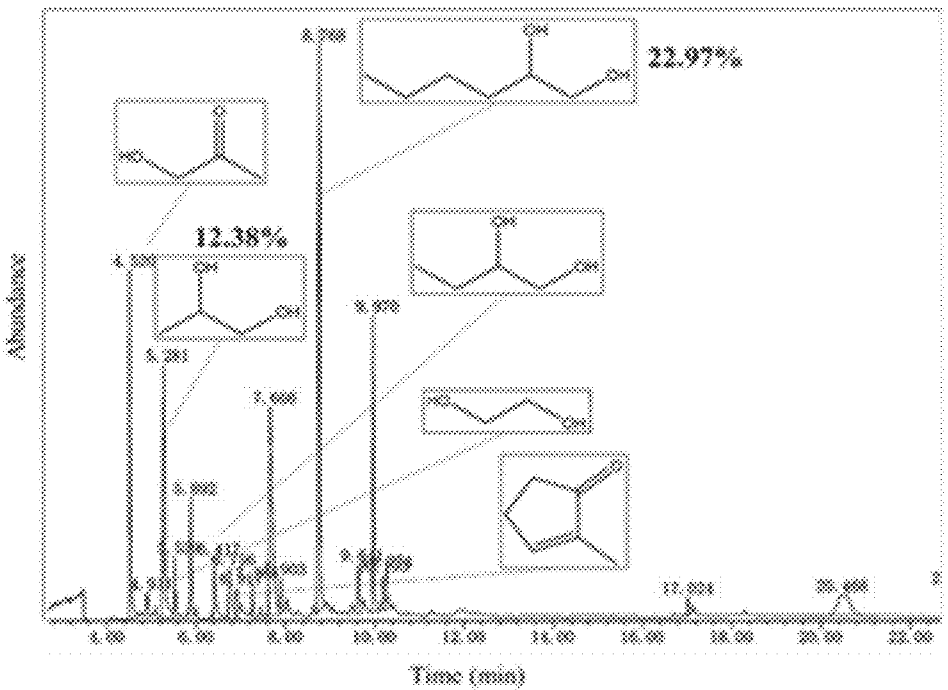
FIG. 9 shows the reaction product distribution of catalytic hydrogenation of glucose using Pt/$SiO_2$ as catalyst in the absence of assistant catalyst in one embodiment.
Figure 10:
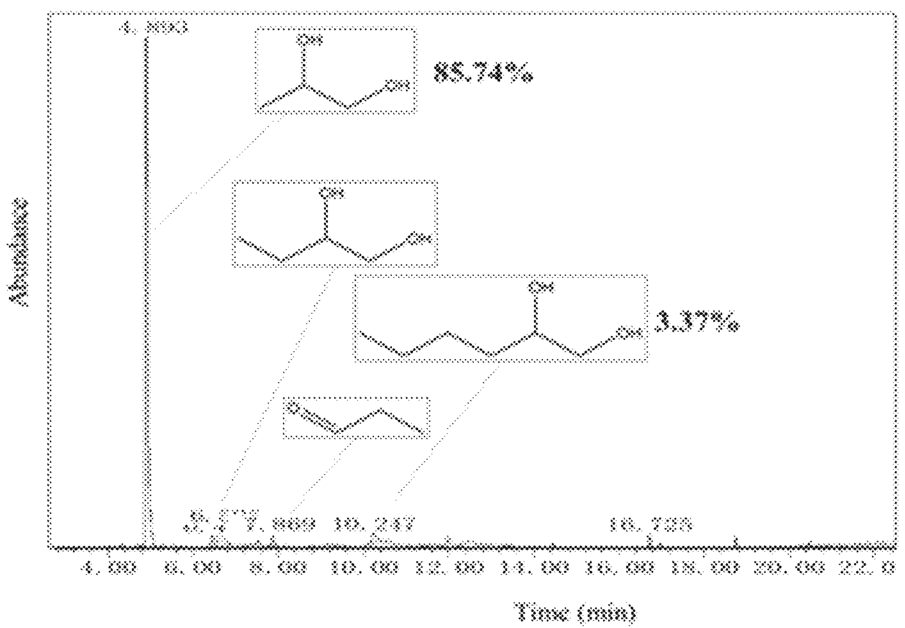
FIG. 10 shows the reaction product distribution of catalytic hydrogenation of glucose using Pt/$SiO_2$ as catalyst in the presence of assistant catalyst in one embodiment.

Please refer to FIG. 9 to FIG. 10. In another embodiment, for example, in a tank reactor, the influence of the presence or absence of the assistant catalyst on the distribution of reaction products of catalytic hydrogenation of glucose by using Pt/$SiO_2$ is investigated. When MgO is absent (as shown in FIG. 9), the reaction products are complex and there are lots of by-products, the peak area of propylene glycol only accounts for 12.38%; when MgO is added (as shown in FIG. 10), the reaction products are extremely single, and the selectivity of propylene glycol is greatly improved, the area of propylene glycol accounts for 85.74%, and the type and amount of by-products are greatly reduced. In addition, the yield of the main by-product 1,2-hexanediol changed significantly before and after the addition of MgO, a peak area of 1,2-hexanediol changes from 22.97% to 3.37%.

In one embodiment, in a tank reactor, the main catalyst and the assistant catalyst of the present application form a composite catalyst. Taking a composite catalyst abbreviated as PtNPs/$SiO_2$@Mg(OH) 2 as an example for illustration, where platinum nanoparticles (PtNPs) is loaded on silica carriers and the main catalyst is coated with a cage-like magnesium hydroxide ($Mg(OH)_2$) shell. The platinum nanoparticles are loaded on the carrier by impregnating a precursor, such as chloroplatinic acid, into the carrier in equal volume, and then aging, drying and calcining; the cage-like magnesium hydroxide shell is formed by adding magnesium oxide to the reaction system and then performing a hydrothermal coating in situ at the same time. By using the catalyst of the present application, sugar biomass can be directionally converted into propylene glycol. The catalyst is simple to synthesize, can realize the in situ loading of assistant catalyst such as magnesium hydroxide, and can make full use of the catalytic activity of the assistant catalyst, such as cage-like magnesium hydroxide, to greatly improve the yield of propylene glycol converted from sugar biomass. For example, in a tank reactor, the assistant catalyst of the present application, such as magnesium hydroxide or magnesium oxide, realizes in-situ hydrothermal coating during the reaction process, which is convenient to operate, directly participates in the reaction after the in-situ hydrothermal loading, avoids the problem of multiple calcinations caused by conventional loading methods and avoids affecting the performance of the original catalyst. A magnesium hydroxide shell with a cage-like shape can be formed through the in-situ loading, and the magnesium hydroxide shell has many advantages, such as its loose structure and its gap, which will not prevent the reactants from reaching the inside of the composite catalyst for catalytic reaction. Compared with the traditional petrochemical route, the method described in this application has the advantages of being green, sustainable, and environmentally friendly, can realize the directional conversion of sugar biomass into propylene glycol, and provides technical support for a new route of industrialization of propylene glycol production.

Figure 12:
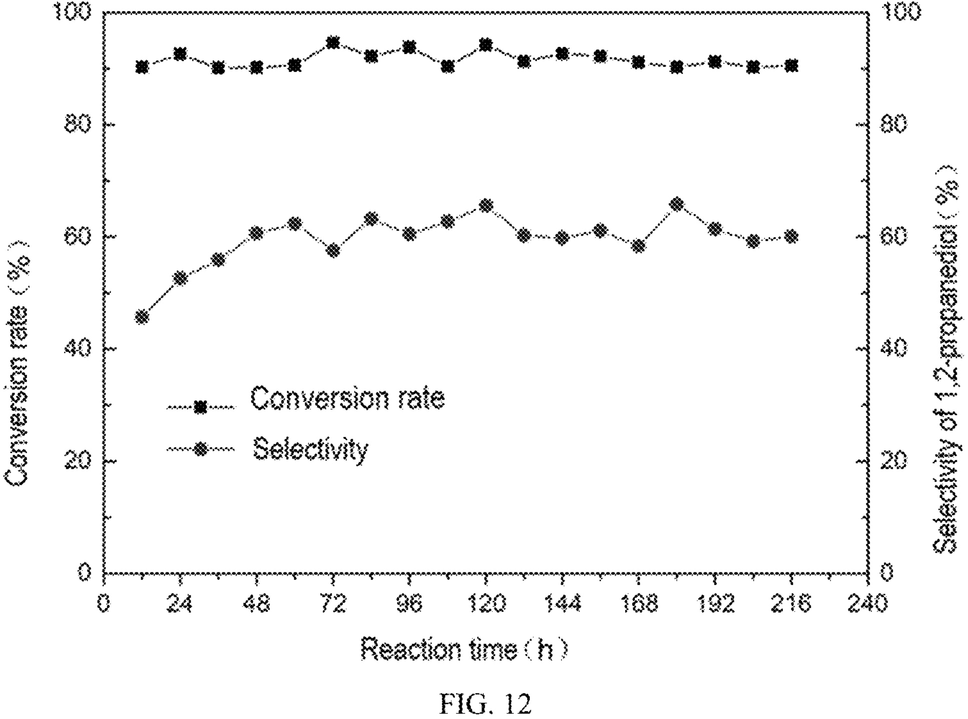
FIG. 12 shows the catalytic effect of PtNPs/$SiO_2$@$Mg(OH)_2$ catalyzing glucose in a fixed bed reactor in one embodiment.

In an embodiment, please refer to FIG. 12, for example, in a fixed bed reactor, the assistant catalyst of the present application is a magnesium hydroxide shell and can combine with the main catalyst to form a composite catalyst with the catalytic activity. The space velocity of the fixed bed reactor ranges from 0.12 $h^{-1}$ to 0.96 $h^{-1}$. In the fixed bed reactor, the sugar includes one or more selected from glucose, sucrose, fructose, trehalose and maltose.

In one embodiment, please refer to FIG. 12, for example, in a fixed bed reactor, 5 g Pt/$SiO_2$ and 0.25 g magnesium oxide powder are mixed and pressed into granules, which are filled into the fixed bed reactor, and the space velocity is $0.12\ h^{-1}$, the reaction temperature is 180° C., 5 wt % glucose solution is employed, and the molar ratio of $H_2$ to glucose is 22.6:1. After operation for more than 200 hours, the conversion rate is maintained above 90%, and the selectivity of 1,2-propanediol is maintained above 50%.

Figure 11:
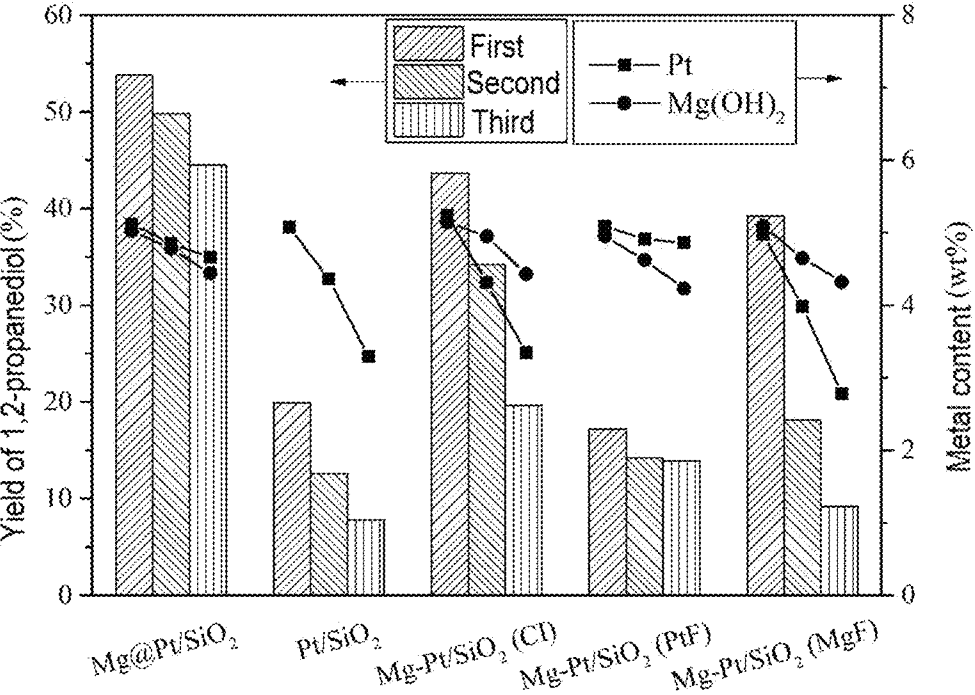
FIG. 11 shows the variations of propylene glycol yield and metal content of the catalyst in three reuse processes of the catalysts synthesized by different methods.

As shown in FIG. 11, the catalyst of the present application has a good recycling effect. For example, the Mg—PtNPs/$SiO_2$ catalyst synthesized in the tank reactor of the present application is compared with the catalysts synthesized through other three commonly used traditional methods. Referring to FIG. 11, it shows variations of propylene glycol yield and metal content in the catalyst during three reuses of catalysts synthesized by different methods. In the figure, Mg—PtNPs/$SiO_2$ shows the changes when using the method described in this application; Mg—Pt/$SiO_2$ (CI) shows the changes when magnesium acetate and chloroplatinic acid are simultaneously impregnated on a $SiO_2$ carrier; Mg—Pt/$SiO_2$(PtF) shows the changes when chloroplatinic acid is first impregnated and calcined, and then magnesium acetate is impregnated; Mg—Pt/$SiO_2$(MgF) shows the changes when magnesium acetate is first impregnated and calcined, and then chloroplatinic acid is impregnated. The propylene glycol yield using the composite catalyst synthesized in the present application after three reuses remains at a relatively high level, while the catalysts synthesized by other methods have their own disadvantages. The main reason is that the composite catalyst synthesized in this application has less metal loss and minimal Pt element loss in reuse, which is due to the fact that the cage-like structure of assistant catalyst such as magnesium hydroxide can restrain Pt nanoparticles in reuse and make it difficult to separate from the catalyst.

Furthermore, it should be understood that the steps or operations mentioned in this specification may be preceded or followed by other steps or that additional steps may be inserted between those mentioned steps, unless otherwise stated. It should also be understood that, unless otherwise specified, the numbering of each step is only to facilitate the identification of the steps, rather than limiting the order of the steps or limiting the scope of the present application. The change or adjustment of the relative order between the steps should also be considered to fall within the scope of this application without changing the substantive technical content.

Finally, it should be noted that the above embodiments are only used to illustrate the technical solutions of the present application, but not to limit the scope of the present application. Although the present application has been described in detail with reference to the foregoing embodiments, those of ordinary skill in the art should understand that: the technical solutions described in the aforementioned embodiments may be modified, or some or all of the technical features may be equivalent replaced, and these modifications or replacements still fall within the scope of this application.

What is claimed is:

1. A composite catalyst, comprising:

a main catalyst; and an assistant catalyst, formed on the main catalyst;

wherein the assistant catalyst is a magnesium hydroxide shell with a cage-like shape on the surface of the main catalyst, and the main catalyst is located inside the magnesium hydroxide shell;

wherein the composite catalyst has a number of basic sites of 0.028-3.14 mmol/g.

2. The composite catalyst according to claim 1, wherein the thickness of the assistant catalyst is 5-20 nanometers.

3. The composite catalyst according to claim 1, wherein active components of the main catalyst comprise one or more selected from platinum nanoparticles, palladium nanoparticles, and rhodium nanoparticles.

4. The composite catalyst according to claim 1, wherein a particle size of active components of the main catalyst is 3-40 nanometers.

5. The composite catalyst according to claim 1, wherein a chemical valence state of active components of the main catalyst is zero.

6. The composite catalyst according to claim 1, wherein a carrier of the main catalyst comprises aluminosilicate molecular sieve, silica, alumina, or zirconia.

7. The composite catalyst according to claim 1, wherein an average pore size of a carrier of the main catalyst is 1-50 nanometers.

8. The composite catalyst according to claim 1, wherein the specific surface area of the composite catalyst is 20-600 $cm^2/g$.

9. The composite catalyst according to claim 1, wherein the magnesium hydroxide is in the form of sheets to coat the main catalyst.

10. A method for preparing propylene glycol, comprising:

mixing a sugar, a main catalyst, and an assistant catalyst in a reactor, then adding a solvent to form a reaction mixture;

performing a hydrothermal reaction in the reactor under a reducing gas atmosphere to obtain the propylene glycol;

wherein the assistant catalyst is a magnesium hydroxide shell with a cage-like shape formed on the surface of the main catalyst, and the main catalyst is located inside the magnesium hydroxide shell to form a main catalyst-assistant catalyst composite catalyst with catalytic activity;

wherein the reactor comprises a tank reactor or a fixed bed reactor;

wherein the sugar in a tank reactor comprises one or more selected from glucose, sucrose, fructose, trehalose, maltose, starch, and cellulose;

wherein the sugar in a fixed bed reactor comprises one or more selected from glucose, sucrose, fructose, trehalose, and maltose.

11. The method according to claim 10, wherein the main catalyst-assistant catalyst composite catalyst has a core-shell structure.

12. The method according to claim 10, wherein the amount of the sugar is 10-22.5 mg/ml based on the volume of the solvent added to the reactor.

13. The method according to claim 10, wherein the temperature of the hydrothermal reaction in the reactor is 140° C.-250° C., and the pressure of the reducing gas atmosphere is 2-6 MPa.

14. The method according to claim 10, wherein the solvent is deionized water.

15. The method according to claim 14, wherein the space velocity in the fixed bed reactor is $0.12\ h^{-1}$ to $0.96\ h^{-1}$.

16. The method according to claim 10, wherein in a tank reactor, the amount of the assistant catalyst is 0.5-2 mg/mL based on the volume of the solvent added to the tank reactor, and the mass ratio of the main catalyst to the assistant catalyst is 10-40:1.

* * * * *